United States Patent [19]

Noah et al.

[11] Patent Number: 5,393,659
[45] Date of Patent: Feb. 28, 1995

[54] AGENT FOR IMMUNOCHEMICAL TESTS WHICH CONTAINS POLYMERS CONTAINING CARBOXYL GROUPS

[75] Inventors: Michael Noah; Rudolf Schmidtberger, both of Marburg, Germany

[73] Assignee: Behringwerke Aktiengesellschaft, Marburg/Lahn, Germany

[21] Appl. No.: 23,154

[22] Filed: Dec. 23, 1992

Related U.S. Application Data

[63] Continuation of Ser. No. 443,312, Nov. 30, 1989, abandoned.

[30] Foreign Application Priority Data

Dec. 2, 1988 [DE] Germany ............................ 3840605.5

[51] Int. Cl.⁶ .................. G01N 33/545; G01N 33/531
[52] U.S. Cl. ................................ 435/7.94; 435/7.92; 435/962; 436/518; 436/531; 436/826
[58] Field of Search ............ 435/7.92, 7.94, 177, 435/180, 962, 967; 436/518, 528, 529, 531, 826, 825; 424/486, 487, 85.8, 88

[56] References Cited

U.S. PATENT DOCUMENTS

| | | | |
|---|---|---|---|
| 4,434,150 | 2/1984 | Azad et al. | 436/518 |
| 4,610,962 | 9/1986 | Takagi et al. | 435/179 |
| 4,870,007 | 9/1989 | Smith-Lewis | 435/28 |

FOREIGN PATENT DOCUMENTS

| | | | |
|---|---|---|---|
| 0163393 | 12/1985 | European Pat. Off. | |
| 245926 | 11/1987 | European Pat. Off. | 435/971 |
| 281251 | 9/1988 | European Pat. Off. | 436/825 |
| 2079936 | 1/1982 | United Kingdom . | |

OTHER PUBLICATIONS

Tanimori, et al. "A Sandwich Enzyme Immunoassay of Rabbit Immunoglobulin G with an Enzyme Labeling Method and a New Solid Support," Journal of Immunological Methods, vol. 62, pp. 123–131, 1983.

King, et al. "Preparation of Protein Conjugates Via Intermolecular Disulfide Bond Formation," Biochemistry, vol. 17, No. 8, pp. 1499–1506, 1978.

*Primary Examiner*—Mary E. Ceperley
*Attorney, Agent, or Firm*—Finnegan, Henderson, Farabow, Garrett & Dunner

[57] ABSTRACT

Agents for immunochemical tests which contain polymers containing carboxyl groups and processes for carrying out such tests are described. These polymers are capable of improving the results obtained with such tests, in that they suppress non-specific reactions and increase the sensitivity of the tests.

8 Claims, No Drawings

AGENT FOR IMMUNOCHEMICAL TESTS WHICH CONTAINS POLYMERS CONTAINING CARBOXYL GROUPS

This application is a continuation, of application Ser. No. 07/443,312, filed Nov. 30, 1989, abandoned.

The invention relates to an agent for the immunochemical detection and for the determination of an analysis substance in a biological material, this agent containing a water-soluble polymer containing carboxyl groups.

Known immunochemical test systems use additives of proteins, polysaccharides and/or surfactants which do not participate in the immunochemical reaction but are suitable for favorably influencing the result of such a reaction.

For immunoassays, for example ELISA, the incubation media required (buffer solutions, incubation medium, conjugate buffer) must be of a composition such that non-specific binding of concomitant substances of the sample and/or conjugate to the solid phase is prevented. The known additives, such as proteins, for example albumin, IgG, casein, hydrolyzed gelatin and derivatives thereof, and mixtures of proteins or human or animal sera as well as surfactants, are therefore used in the incubation media.

An incubation medium for solid phase immunochemical tests which contains lactoferrin, fetal calf serum, polyoxyethylene 20-sorbitan monolaurate ($^R$Tween 20) and buffer salts is described in German Patent 3,638,767.

Additives comprising surfactants from the poloxamer group, for example $^R$Pluronic F 68, and from the poloxamine group, for example $^R$Tetronic 707 and 1107, are also described in European Patent A-215,457, the three compounds mentioned proving to be advantageous in comparison wither ween $^R$Tween 20.

However, incubation media provided with these additives cannot prevent incorrect measurement values which occur, for example, in one-step sandwich tests which use large sample volumes at high conjugate concentrations but low conjugate volumes in order to achieve optimum sensitivity.

There was therefore the object of discovering an agent with which incorrect measurement values can be prevented by incubation with the sample.

It has been found, surprisingly, that water-soluble polymers containing carboxyl groups are even more suitable than additives of the prior art for preventing incorrect measurement values and favorably influencing an immunochemical reaction, which has the effect of a higher sensitivity of the detection and determination of an analysis substance contained in a biological material, which is also to be referred to as the sample.

These polymers, as a constituent of such an agent, can already be present during preparation of the sample for the test.

The invention thus relates to an agent for the detection or determination of an analysis substance in a biological material containing immunochemical reactants, at least one of which reacts with the analysis substance, which moreover contains a water-soluble polymer containing carboxyl groups.

Suitable water-soluble polymers containing carboxyl groups can be prepared from water-insoluble synthetic polymers which carry ester or anhydride groups, by alkaline hydrolysis. Such water-insoluble polymers are known. Examples of these are polymers which are prepared using, as monomers, esters of acrylic acid and alkylacrylic acid or maleic anhydride, by themselves or as a mixture with monomers containing no carboxyl groups (for example methyl vinyl ether, styrene, ethylene, propylene or octadecene). These polymers, referred to as homopolymers or as heteropolymers, are in general obtained by free radical polymerization, that is to say by addition of free radical initiators, for example by means of coumaryl hydroperoxide or by means of dibenzoyl peroxide, the chain length of the polymer being controlled by the amount of peroxide added, or by the temperature or the addition of a telogen, for example carbon tetrachloride or an agent which collects free radicals, for example N-acetylcysteine or another thiol.

Reaction products of molecular weight greater than 2000 are in general referred to as polymers, and those products having a molecular weight of less than 2000 are referred to as oligomers or telomers.

Water-soluble synthetic heteropolymers containing carboxyl groups are successfully prepared only if the ratio of monomer carrying carboxyl groups and monomers which contain no carboxyl groups is chosen so that the resulting polymer, oligomer or telomer is water-soluble following alkaline hydrolysis. This ratio can be determined empirically for each heteropolymer. For example, whereas a heteropolymer prepared from the monomers styrene and maleic anhydride at a molar ratio of 2 to 2.5:1 is still water-soluble after alkaline hydrolysis, at a ratio above 3:1 it remains water-insoluble after alkaline hydrolysis. Water-soluble polypeptides, containing carboxyl groups, which contain aspartic acid, glutamic acid and if appropriate also neutral aminoacids, which are commercially available or can be prepared by known methods of peptide synthesis, are also suitable.

The polysaccharides which are obtainable from natural products and contain sugar acids, for example pectic acid and galacturonic acid, are moreover suitable.

The following polymers are preferred:

Polyacrylic acid, polymaleic acid, polymers or telomers of maleic anhydride and methyl vinyl ether or ethylene or propylene or octadecene, the anhydride rings of which are opened by hydrolysis, polyaspartic acid, polyglutamic acid and polygalacturonic acid.

Telomers of maleic anhydride and methyl vinyl ether or propylene which are converted into the water-soluble carboxyl-containing polymers by treatment with sodium hydroxide solution are particularly preferred.

A large number of agents containing immunochemical reactants and/or binding partners of bioaffinity are known.

The agents are in general named according to the immunochemical processes for which they are used.

Agents in the sense of the invention are those with which precipitates as a dispersion or in a gel or agglutinates of particles are produced, or absence thereof is effected, or those in which a color signal or radiation is produced or prevented by the immunochemical reaction.

Agents from the group mentioned last which are preferred are those with which solid phase immunochemical tests which are called ELISA (enzyme linked immunosorbent assay) or scintillation assay if a coloration or radiation is produced from an enzyme substrate, solid phase radioimmunoassay if radiation is produced by a radioactively labeled isotope, or solid phase fluorescence assay if fluorescence is produced by a fluorogen.

Diagnostic agents contain antigens, antibodies or both at the same time as reactants and other binding partners for the reactants or of bioaffinity to the analysis substance, for example lectins, complement, protein A or G and derivatized biotin and avidin, it being possible for at least one of the reactants to be labeled, and if appropriate reagents for detection of the labeling. One of the reactants can moreover be present as a solid phase.

A solid phase in the sense of the invention is a water-insoluble carrier to which one or more reactants are bonded.

Examples of carriers are latex particles, granular, swellable or non-swellable material, beads, internal surfaces of tubes, microtest plates as a particular embodiment of an arrangement of tubes and also porous materials to be described as an absorbent matrix.

One constituent of the agent according to the invention can be a device for accommodating a sample, for example a vessel for accommodating a sample or the uptake zone, for example an absorbent matrix, for the sample on a so-called "dry chemical" test system. The constituent can also be an aqueous solution which also contains buffer salts and if appropriate stabilizing additives, such as proteins or polysaccharides, as substances which likewise stabilize the analysis substance, the polymer being present in a concentration of 0.01 to 50 g/l, preferably 0.1 to 20 g/l and particularly preferably 0.2 to 2 g/l.

The polymer can also be contained in a device as a constituent of the diagnostic agent in which the immunochemical reaction takes place.

The biological materials also called the sample which contain the analysis substances are, for example, tissue from biopsis or autopsies, blood, blood cells, serum or plasma, secretions, fluid from an inflamed or non-inflamed tissue, the disintegration products of tissue and metabolic excretions.

The invention moreover relates to a process for the immunochemical determination of an analysis substance contained in a biological material, which comprises bringing the analysis substance together with the polymer, if appropriate incubating the mixture in an aqueous solution and performing an immunochemical determination with the mixture obtained in this way.

The invention furthermore relates to the use of such a polymer in immunochemical tests.

The biological materials are brought together with the polymer and can be stored in this way for a prolonged period of time without the analysis substance contained therein changing in its immunochemical properties.

Immunochemical processes in which one of the reactants is present in a solid phase, the treated material described above being brought together with the solid phase, if appropriate together with other immunochemical reactants, apart from those of the solid phase and reagents for detection of the analysis substance, the solid phase then being separated from the liquid phase and the analysis substance being determined either in the solid or in the liquid phase, are preferred.

EXAMPLES

1. Preparation of water-soluble carboxyl-containing polymers 1.1 Carboxylate of maleic anhydride-propylene telomer (MPT carboxylate)

5 g of MPT 155, a commercial product from Stickstoffwerke Linz, were suspended in 500 ml of deionized water. 13 ml of 5 normal sodium hydroxide solution were then added dropwise in the course of one hour, while stirring. The mixture was stirred for a further 3 hours, a pH of 8 being maintained by further addition of 1 normal sodium hydroxide solution. The solution obtained in this way was left to stand at 20°–25° C. for a further 15 hours before it was used further.

1.2 Carboxylate of maleic anhydride-methyl vinyl ether telomer (MMVT carboxylate) 5 g of a maleic anhydride-methyl vinyl ether telomer obtainable under the name Gantrez AN179 from Serva, Heidelberg, were treated as described in 1.1.

2. Preparation of constituents of test kits for determination of hepatitis B surface antigen (HBs) by the solid phase 2-side immunochemical process (sandwich ELISA)

2.1 Microtest plates coated with antibodies against HBs

Microtest plates, that is to say immunoplates II 96 F with round bases (Nunc, Roskilde, Denmark, Article No. 262162) were coated with monoclonal anti-HBs and immunoglobulin G (IgG) from mice. For this, the IgG was diluted to 2 mg/l in 100 mmol/l sodium bicarbonate of pH 9.6. 100 µl of the dilution was introduced into each depression (well) of the microtest plates. The test plates filled in this way were left at 20° C. for 18 hours and were then washed 3–4 times with 200 µl of a solution of 1 g/l of $^R$Tween 20 in phosphate-buffered physiological saline solution, pH 7.4, by filling and suction, and the test plates were then dried over silica gel at 20° C.

2.2 Anti-HBs IgG peroxidase conjugate

Monoclonal mouse IgG, directed towards HBs, was reacted with N-gamma-maleimidobutyryl oxysuccinimide (GMBS) as described by Tanamori et al., 1983 in J. Immunol. Meth. 62, 123–131. 2-Iminothiolane hydrochloride (Sigma, Catalog No. I 6256) was reacted with horseradish peroxidase (POD), obtained from Boehringer Mannheim, Catalog No. 413470, as described by King et al. 1978 in Biochem. 17, 1499–1506. An IgG-POD conjugate was prepared from the GMBs-IgG conjugate and the immunothiolane-POD conjugate as described by Tanamori. The resulting solution of the IgG-POD conjugate had a protein content of 1.2 mg/ml. The ratio of POD to IgG was determined as 2.5. The solution was then diluted to 24 and 6 µg/ml of IgG-POD with a solution which contained 200 ml/l of bovine serum defibrinized and delipidized by heating, 1 g/l of $^R$Polygeline, 50 mmol/l of tris, 150 mmol/l of trisodium citrate and 0.5 mol/l of NaCl, brought to pH 7.4 with HCl and the resulting solutions were called 24 µl/ml and 6 µg/ml of anti-HBs-POD.

2.3 TMB substrate preparation

To detect anti-HBs-POD, a substrate system or a substrate preparation containing hydrogen peroxide and tetramethylbenzidine (TMB) prepared from two stock solutions was used.

Stock solution 1: TMB dihydrochloride was dissolved in doubly distilled water in a concentration of 5 g/l, that is to say 16 mmol/l while stirring, and the solution was brought to pH 1.5 with 5 normal hydrochloric acid. Penicillin G was added to this solution in a final concentration of 200 mg/l that is to say 0.56 mmol/l while stirring.

Stock solution 2: 1.4 ml of glacial acetic acid, 1.5 ml of 1 normal NaOH and 250 mg, that is to say 3 mmol, of $H_2O_2$ as a urea-hydrogen peroxide adduct were added to 900 ml of doubly distilled water. After the components had dissolved completely, the solution was made up to 1 with doubly distilled water.

TMB substrate preparation: One part by volume of stock solution 1 and 10 parts by volume of stock solution 2 were mixed with one another.

3. Comparative determinations and results 3.1 Determination of HBs by one-step sandwich ELISA Some sera which had been determined as HBs-negative by the process of the prior art, that is to say the two-step sandwich ELISA, but were not to be evaluated unambiguously in the one-step sandwich ELISA without using a polymer containing carboxyl groups because they produced extinctions greater than 0.04 were included in the determination. Since all the samples of a reference panel classified as HBs-negative produced extinctions of less than 0.040 in the two-step sandwich ELISA, this ELISA was evaluated as reliable in respect of avoiding falsely positive results. A negative and a positive control were also run in the determination. 2 depressions of a microtest plate which had been coated with antibodies against HBs as described under 2.1 were used for each control and for each sample. 25 $\mu$l of a solution of 24 $\mu$g/ml of anti-HBsPOD and 25 $\mu$l of this solution with the addition of 1 g/l of MMVT carboxylate were used in groups of 2 depressions. Either 100 $\mu$l of negative or 100 $\mu$l of positive control or 100 $\mu$l of sample were introduced per depression of each group.

The microtest plate treated in this manner was left to stand at 37° C. for 1 hour. The contents of the depressions were then removed by suction and the depressions were washed 4 times with in each case 200 $\mu$l of a solution of 1 g/l of $^R$Tween 20 in phosphate-buffered physiological saline solution, pH 7.4, by filling and suction. 100 $\mu$l TMB substrate preparation were introduced into each depression and left to stand at 20–22° C. for 30 minutes, and 100 $\mu$l of 1 normal sulfuric acid were then added. The extinctions of the solutions in the depressions were measured at 450 mm against a blank value of 200 $\mu$l of phosphate-buffered saline solution in a further depression.

3.2 Determination of HBs by the two-step sandwich ELISA, a process of the prior art 100 $\mu$g of negative control, 100 $\mu$l g of positive control and 100 g of the samples which were also tested in the one-step sandwich were introduced into depressions of a microtest plate coated with antibodies against HBs in accordance with Example 2.1. The plate was left to stand at 37° C. for 1 hour. The contents of the depressions were then washed 4 times, as described in Example 3.1. 100 $\mu$l of a solution of 6 $\mu$g/ml of anti-HBs-POD were then added and the plate was left to stand again at 37° C for 1 hour. The contents of the depressions were removed and the depressions were washed, as described above. The addition of TMB substrate preparation and of sulfuric acid and the measurement of the extinction of the solutions in the depressions were carried out in the same manner as described in Example 3.1.

3.3 Measurement results of the determinations of HBs in accordance with Examples 3.1 and 3.2.

The extinctions obtained from the negative and the positive control and from 10 serum samples by the one-step and two-step sandwich ELISA are shown in the table. Values for the upper limit, called the "cut-off" of the extinction of samples to be classified as HBs-negative are also given. The "cut-off" was specified as the extinction of the negative control plus an extinction of 0.025.

It can be seen from the table that the one-step sandwich assay gives higher extinctions for the positive control than the two-step sandwich ELISA, but that the samples determined as negative in the two-step assay appear as positive in the one-step assay if the solution which contains the HBs-POD conjugate contains no addition of MMVT carboxylate.

The one-step sandwich ELISA described containing MMVT carboxylate is reliable, at a high sensitivity, in respect of the decision of whether a sample is to be classified as HBs-negative, because the extinctions measured are all below 0.040, the "cut-off", and are not about at 0.040.

In further experiments, it was found that one-step sandwich ELISAs for detection of HBSs which contain MPT carboxylate, polyacrylic acid, polyaspartic acid and/or polygalacturonic acid give equivalent results.

TABLE

| | Sandwich - ELISA | | |
|---|---|---|---|
| | One-step with MMVT carboxylate | One-step | Two-step |
| | Extinctions at 450 nm | | |
| negative control | 0.015 | 0.014 | 0.019 |
| cut-off | 0.040 | 0.039 | 0.044 |
| positive control | 1.692 | 1.514 | 0.918 |
| HBs-negative sera | | | |
| 1 | 0.018 | 0.281 | 0.038 |
| 2 | 0.011 | 0.076 | 0.018 |
| 3 | 0.008 | 0.072 | 0.028 |
| 4 | 0.005 | 0.024 | 0.023 |
| 5 | 0.007 | 0.128 | 0.028 |
| 6 | 0.020 | 0.017 | 0.025 |
| 7 | 0.030 | 0.011 | 0.017 |
| 8 | 0.036 | 0.049 | 0.015 |
| 9 | 0.010 | 0.056 | 0.029 |
| 10 | 0.036 | 0.015 | 0.026 |

We claim:

1. An agent for the immunochemical detection or determination of an analysis substance in a sample of biological material comprising:
    (a) at least one immunochemical reactant being capable of reacting with the analysis substance and being bonded to a solid phase; and
    (b) an aqueous solution of a water-soluble polymer containing carboxyl groups selected from the group consisting of polyacrylic acid, polymaleic acid, polymers or telomers of maleic anhydride and methyl vinyl ether or ethylene or propylene or octadecene, the anhydride rings of which are opened by hydrolysis, and polygalacturonic acid, said polymer being present in said aqueous solution in a concentration of 0.1 to 50 g/L.

2. An agent as claimed in claim 1, wherein the polymer containing carboxyl groups is polyacrylic acid.

3. An agent as claimed in claim 1, wherein the polymer containing carboxyl groups is obtained by alkaline hydrolysis of maleic anhydride-propylene polymer.

4. An agent as claimed in claim 1, wherein the polymer containing carboxyl groups is obtained by alkaline hydrolysis of maleic anhydride-methyl vinyl ether polymer.

5. An agent for the immunochemical detection or determination of an analysis substance in a sample of biological material comprising:
   (a) dry chemical test device coated with a water-soluble polymer containing carboxyl groups selected from the group consisting of polyacrylic acid, polymaleic acid, polymers or telomers of maleic anhydride and methyl vinyl either or ethylene or propylene or octadecene, the anhydride rings of which are opened by hydrolysis, and polygalacturonic acid, said device having been coated with said polymer in a concentration of 0.1 to 50 g/L; and,
   (b) at least one immunochemical reactant being capable of reacting with the analysis substance.

6. A process for the immunochemical determination of an analysis substance contained in a sample of biological material, which comprises the steps of:
   (a) applying an aqueous solution containing the analysis substance and a water-soluble polymer containing carboxyl groups selected from the group consisting of polyacrylic acid, polymaleic acid, polymers or telomers of maleic anhydride and methyl vinyl ether or ethylene or propylene or octadecene, the anhydride rings of which are opened by hydrolysis, and polygalacturonic acid, said polymer being present in a concentration of 0.01 to 50 g/L, to an immunochemical reactant present on a solid phase and being capable of reacting with the analysis substance;
   (b) separating the solid phase from the liquid phase; and
   (c) determining the analysis substance either in the solid phase or in the liquid phase by using an immunochemical reactant carrying a detectable label.

7. A process for the immunochemical determination of an analysis substance contained in a sample of biological material, which comprises the steps of:
   (a) applying an aqueous solution containing the analysis substance and a water-soluble polymer containing carboxyl groups, present in a dry form before addition to the aqueous solution, selected from the group consisting of polyacrylic acid, polymaleic acid, polymers or telomers of maleic anhydride and methyl vinyl either or ethylene or propylene or octadecene, the anhydride rings of which are opened by hydrolysis, and polygalacturonic acid, in a concentration of 0.01 to 50 g/L in the aqueous solution, to an immunochemical reactant capable of reacting with the analysis substance and present on a solid phase; and,
   b) determining the amount of analysis substance bound to the immunochemical reactant.

8. A process for the immunochemical determination of an analysis substance contained in a sample of biological material, which comprises the steps of:
   (a) adding to an aqueous solution containing the analysis substance a dry chemical test device coated with a water-soluble polymer containing carboxyl groups selected from the group consisting of polyacrylic acid, polymaleic acid, polymers or telomers of maleic anhydride and methyl vinyl ether or ethylene or propylene or octadecene, the anhydride rings of which are opened by hydrolysis, and polygalacturonic acid, said device having been coated with said polymer in a concentration of 0.01 to 50 g/L; and an immunochemical reactant present on a solid phase and being capable of reacting with the analysis substance;
   (b) separating the solid phase from the liquid phase; and
   (c) determining the analysis substance either in the solid phase or in the liquid phase by using an immunochemical reactant carrying a detectable label.

* * * * *

UNITED STATES PATENT AND TRADEMARK OFFICE
CERTIFICATE OF CORRECTION

PATENT NO. : 5,393,659
DATED : February 28, 1995
INVENTOR(S) : Michael NOAH et al It is certified that error appears in the above-indentified patent and that said Letters Patent is hereby corrected as shown below:

Claim 5, Column 7, Line 10, "either" should read --ether--.

Claim 7, Column 8, Line 10, "either" should read --ether--.

Signed and Sealed this

Eleventh Day of July, 1995

Attest:

BRUCE LEHMAN

Attesting Officer        Commissioner of Patents and Trademarks